(12) United States Patent
Bouyssou et al.

(10) Patent No.: US 6,429,229 B1
(45) Date of Patent: Aug. 6, 2002

(54) KETO ACID SALTS AND AMINE DERIVATIVES, AND THEIR USE FOR PREPARING MEDICINES

(75) Inventors: Thierry Bouyssou, Beynes; Serge Biosa, Mantes la Jolie; Pierre-Andre Settembre, Houilles; Christian Jeanpetit, Bougival, all of (FR)

(73) Assignee: Chiesi S.A., Courbevoie (FR)

( * ) Notice: Subject to any disclaimer, the term of this patent is extended or adjusted under 35 U.S.C. 154(b) by 0 days.

(21) Appl. No.: 09/646,059

(22) PCT Filed: Mar. 11, 1999

(86) PCT No.: PCT/FR99/00545

§ 371 (c)(1),
(2), (4) Date: Nov. 13, 2000

(87) PCT Pub. No.: WO99/47134

PCT Pub. Date: Sep. 23, 1999

(30) Foreign Application Priority Data

Mar. 13, 1998 (FR) ............................................. 98 03155

(51) Int. Cl.$^7$ ................................................. A61N 37/12
(52) U.S. Cl. ........................ 514/561; 514/564; 514/574; 514/562; 514/553; 514/424; 514/319
(58) Field of Search ...................... 562/553; 424/319; 514/561, 564, 574

(56) References Cited

U.S. PATENT DOCUMENTS 4,320,146 A * 3/1982 Walser et al.
4,734,276 A * 3/1988 Ziegler et al.
4,957,938 A * 9/1990 Anderson et al.

FOREIGN PATENT DOCUMENTS

FR 3533 * 10/1965

OTHER PUBLICATIONS

Aldrich Catalog, Handbook of Fine Chemicals, 1996–1997.*

* cited by examiner

Primary Examiner—Paul J. Killos
Assistant Examiner—Hector M Reyes
(74) Attorney, Agent, or Firm—Young & Thompson

(57) ABSTRACT

The invention concerns the use of compounds of general formula (I): $(X)_{n1},Y,(Z)_{n2}$ wherein n1 and n2 represent 0 or 1; X represents a natural amino acid, in particular an amino acid selected among ornithine, arginine, lysine, histidine or glutamine; Y represents a keto acid of formula (II): R—CO—COOH wherein R represents —$CH_3$, —$CH_2$—$CH_3$, —$CH(CH_3)_2$, —$CH(CH_3)$—$CH_2$—$CH_3$, —$CH_2$—$CH(CH_3)_2$, —$(CH_2)_2$—COOH, —$(CH_2)_3$—COOH; Z represents: a natural amino acid selected in particular among ornithine, arginine, lysine, histidine or glutamine; or a polyamine selected in particular among cadaverine, putrescine, spermidine, spermine or agmatine. Said compounds are useful for preparing a medicine for treating human or animal pathologies wherein are involved silent neurons, such as pathologies of the digestive tract, the bladder and the biliary ducts.

13 Claims, No Drawings

KETO ACID SALTS AND AMINE DERIVATIVES, AND THEIR USE FOR PREPARING MEDICINES

The present invention has for its objects salts of keto acids and of amine derivatives, as well as their use for the preparation of pharmaceutical compositions for the treatment of pathologies in which are involved silent neurons.

The nociceptive message results from the intense activation of the free terminals (nociceptors) of the C and Aδ fibers which under physiological conditions take part in the regulation of the function of the organs. These fibers are contained in the cutaneous, muscular and articular tissues as well as in the walls of the viscera.

In the digestive tract as well as in the bladder and the biliary ducts, this nerve structure cohabits with a population of silent neurons (Mayer, E. A.; Gebhart, G. F.; Gastroenterology, 1994, 107, 271–293) whose expression appears only in the presence of an inflammatory or nervous lesion.

This physiopathological mechanism inspired the creation of the model of distension of the colon first irritated with 1% acetic acid, in rat. This model is hence representative of the illnesses of digestive origin and is used particularly for detecting compounds active in the treatment of the irritable intestine syndrome (IIS). IIS is characterized by the presence of abdominal pain. Patients having this pathology have a lowered threshold of digestive sensitivity.

Morphine is active on the model of colic distension whilst the classical analgesics (AINS, aspirin, paracetamol) are inactive in the test. They are on the other hand active in the "writhing test" (model of visceral pain in which the silent neurons are not involved) which is effected by intraperitoneal injection of phenylbenzoquinone or 3% acetic acid in rat or a mouse. Morphine is hence capable of modifying the reactivity of the silent nociceptors, which AINS cannot do.

Similarly, one opinion, described in JP 43-05524 as an analgesic, is active in the "writhing test" at 500 and 1000 mg/kg by intravenous route in mice. It is also active in a somatic pain test in which the silent neurons are not involved (Kawabata, Atsugumi et coll., Eur. J. Pharmacol., 1996, 296 (1), 23–31), at doses between 300 and 1000 mg/kg by subcutaneous route in rat.

By contrast, it is inactive in the model of colic distension in rat at doses of 1 to 20 mg/kg by oral route (Table I). Ornithine is thus not capable of modifying the reactivity of the silent nociceptors at these dosages.

Moreover, J. Goldhill et coll. (Gastroenterology, April 1996, 110 (4), abstract A916) have shown that glutamine is active in the test of colic distension at a dose of 6 mg/kg by rectal route in rat (local administration on the irritated colic mucosa).

Finally, α-ketoglutarate of di-ornithine is used in therapy (French patent 3 533 M) to improve the proteic metabolism of starved subjects. It is also known as a hormonal stimulant (growth hormone and insulin) and stimulating cellular growth.

The present invention follows from the discovery by the inventors, of the fact that salts of the general formula (I):

$$(X)_{n1}, Y, (Z)_{n2} \quad (I)$$

in which:
X is an amino acid;
Y is a keto acid;
Z is an amino acid or a polyamine,
$n_1$ and $n_2$ represent 0 or 1, provided that when $n_1=0$ then $n_2=1$, and when $n_2=0$, $n_1=1$, have the property of increasing the threshold of perception of digestive pain and as a result are capable of modifying the reactivity of the silent nociceptors in an amount at least 1 mg/kg by oral route.

This discovery is the more unexpected, because the keto acids separately tested are inactive. The separately tested amino acids are also inactive or active at higher dosages (see Table I hereafter).

The activity of these salts is not due to the keto acid alone or to the amino acid alone, but to the synergy between these two types of compounds.

Thus, by way of illustration, Table I shows nicely that:
- the comparisons 1 and 2 are inactive whilst the compounds of Examples 1 and 2 (salts between comparisons 1 and 2) are active at 1 mg/kg;
- comparison 3 is inactive whilst the compound of Example 6 (salt between comparisons 3 and 2) is also active from 1 mg/kg;
- comparison 4 is active at 10 mg/kg whilst the compound of Example 5 (salt between comparisons 1, 2 and 4) is active from 1 mg/kg;
- comparison 5 is active only from 20 mg/kg whilst the compounds of Examples 3 (salts of comparisons 1 and 5) and 4 (salts of comparisons 1, 2 and 5) are active from 10 mg/kg.

The present invention has for its object the use of compounds of the following general formula (I):

$$(X)_{n1}, Y, (Z)_{n2} \quad (I)$$

in which:
$n_1$ and $n_2$ are 0 or 1, provided that when $n_1=0$ then $n_2=1$, and when $n_2=0$ then $n_1=1$,
X is a natural amino acid, provided that when $n_2 0$ then X is a basic amino acid such as:
ornithine,
arginine,
lysine,
or, histidine,
Y is a keto acid of the following formula (II):

$$R-CO-COOH \quad (II)$$

in which R is an alkyl or alcanolic acid group, substituted or not, from about 1 to about 10 carbon atoms, particularly a keto acid of formula (II) in which when R is:
—$CH_3$, said keto acid is pyruvic acid,
—$CH_2$—$CH_3$, said keto acid is α-ketobutyric acid,
—$CH(CH_3)_2$, said keto acid is α-ketoisovaleric acid,
—$CH(CH_3)$—$CH_2$—$CH_3$, said keto acid is β-methylvaleric α-keto acid,
—$CH_2$—$CH(CH_3)_2$, said keto acid is α-keto isocaprilic acid,
—$(CH_2)_2$—COOH, said keto acid is α-keto glutaric acid,
—$(CH_2)_3$—COOH, said keto acid is α-keto adipic acid,
Z represents:
a natural amino acid, particularly an amino acid selected from ornithine, arginine, lysine, histidine or glutamine,
or, a polyamine comprising at least two primary, secondary or tertiary amine functions, spaced by a linear or branched hydrocarbon chain of about 3 to 10 carbon atoms, particularly a polyamine of the following formula (III):

$R_1$—HN—$(CH_2)_n$-NH—$R_2$ (III)

in which:
n represents a whole number comprised between 4 and 5, and when n=4,
$R_1$ and $R_2$ are H,
or, $R_1$ is H and $R_2$ is $(CH_2)_3NH_2$,
or, $R_1$ and $R_2$ are $(CH_2)_3NH_2$, when n=5,
$R_1$ and $R_2$ are H,

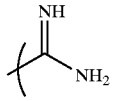

or, $R_1$ is H and $R_2$ is a group of the formula particularly a polyamine selected from cadaverine, putrescine, spermidine, spermine or agmatine, for the preparation of a medication adapted for the treatment of human or animal pathologies in which are involved the silent neurons, such as pathologies of the digestive tract, of the bladder and of the biliary ducts.

Of course, the compounds of formula (I) above result from the formation of principally ionic bonds, and in no case of covalent bonds, between the different constituents X, Y or Z. As a result, the order of appearance of the different constituents in formula (I) has no particular significance, and this formula (I) should be understood to comprehend also the compounds of the formula $(X)_{n1}$, Y, $(Z)_{n2}$ those of formula $(Z)_{n2}$, Y, $(X)_{n1}$; $(X)_{n1}$, $(Z)_{n2}$, Y; $(Z)_{n2}$, $(X)_{n1}$, Y; Y, $(X)_{n1}$, $(Z)_{n2}$; Y, $(Z)_{n2}$, $(X)_{n1}$.

Preferably, the invention has for its object the above-mentioned use of compounds of formula (I) as defined above, in which Y is a keto acid selected from α-ketoglutaric acid, or α-ketobutyric acid.

The invention has more particularly for its object the above-mentioned use, of compounds of formula (I) in which:

$n_1$=1, and $n_2$=0 or 1,

X is an amino acid selected from ornithine, arginine or glutamine,

Y is a keto acid selected from α-ketoglutaric acid, or α-ketobutyric acid, and, when $n_2$=1, Z is:
a natural amino acid, particularly ornithine, arginine or glutamine,
or a polyamine of the above formula (III) such as cadaverine, putrescine, spermidine, spermine or agmatine.

Compounds of formula (I) in which $n_1$=1, and $n_2$=0, particularly preferred for their use in the field of the present invention, are those in which:

X is ornithine and Y is α-ketoglutaric acid, namely mono-ornithine α-ketoglutarate, X is ornithine and Y is α-ketobutyric acid, namely mono-ornithine α-ketobutyrate, or those in which:
X is arginine and Y is α-ketobutyric acid, namely arginine α-ketobutyrate,
X is lysine and Y is α-ketobutyric acid, namely lysine α-ketobutyrate,
X is histidine and Y is α-ketobutyric acid, namely histidine α-ketobutyrate, X is arginine and Y is α-ketoisocaproate acid, namely arginine α-ketoisocaproate,
X is ornithine and Y is α-ketoisocaproate acid, namely ornithine α-ketoisocaproate,
X is ornithine and Y is α-keto-β methylvalerate acid, namely ornithine α-keto-β methylvalerate,
X is arginine and Y is α-keto-β methylvalerate acid, namely arginine α-keto-β methylvalerate,
X is arginine and Y is α-keto-isovaleric acid, namely arginine α-keto-isovalerate,
X is ornithine and Y is α-keto-isovaleric acid, namely ornithine α-keto-isovalerate.

Compounds of the formula (I) in which $n_1$=1, and $n_2$=1, particularly preferred for their use in the field of the present invention, are those in which:

X is ornithine, Y is α-keto-glutaric acid, and Z is ornithine, namely diornithine α-keto-glutarate,
X is arginine, Y is α-keto-glutaric acid, and Z is arginine, namely diarginine α-keto-glutarate,
X is ornithine, Y is α-keto-glutaric acid, and Z is arginine, namely ornithine and arginine α-keto-glutarate,
X is ornithine, Y is α-keto-glutaric acid, and Z is glutamine, namely ornithine and glutamine α-keto-glutarate,
X is ornithine, Y is α-keto-glutaric acid, and Z is spermidine, namely ornithine and spermidine α-keto-glutarate.

Preferably, the compound used in the present invention is di-ornithine α-keto-glutarate.

The invention has more particularly for its object the above-mentioned use, of compounds of the formula (I) in which:

$n_1$=0 or 1, and $n_2$=1, when $n_1$=1, X is a natural amino acid, such as ornithine, arginine or glutamine, Y is a keto acid selected from α-keto-glutaric acid, or α-keto-butyric acid, Z is a polyamine of the above formula (III) such as cadaverine, putrescine, spermidine, spermine or agmatine.

A compound of formula (I) in which $n_1$=0, and $n_2$=1, particularly preferred for its use in the field of the present invention, is that in which Y is α-keto-glutaric acid and Z is spermidine, namely spermidine α-keto-glutarate.

The invention also has for its object compounds of the following general formula (IV):

$(X)_{na}$, $(Y)_{nb}$, Z (IV)

in which:
$n_a$ and $n_b$ are 0 or 1, provided that when $n_a$=0 then $n_b$=1 and when $n_b$=0 then $n_a$=1, X is a natural amino acid, particularly a basic amino acid such as ornithine, arginine, lysine or histidine, Y is a keto acid of the above formula (II), Z is a polyamine comprising at least two primary, secondary or tertiary amine functions, spaced by a linear or branched hydrocarbon chain of about 3 to 10 carbon atoms, particularly a polyamine of the above formula (III), such as cadaverine, putrescine, spermidine, spermine or agmatine.

The invention more particularly has for its object the compound of general formula (IV) in which $n_a$=0 and $n_b$=1, Y is α-keto-glutaric acid and Z is spermidine, and corresponding to the compound of formula (I) in which $n_1$=0 and $n_2=1$, Y is α-keto-glutaric acid and Z is spermidine, namely spermidine α-keto-glutarate.

Preferably, the compounds as described above are present in the form of salts between two constituents X and Y, or Y and Z, or between the three constituents X, Y and Z.

The weight proportion of the various constituents is preferably comprised between 0.8 and 1.2, such that the sum of the proportions of each of the constituents is equal to 2 in the case of a salt between two constituents X and Y, or Y and Z, or is equal to 3 in a salt between three constituents X, Y and Z.

Preferably, the above-mentioned proportion of the different constituents is comprised between 0.9 and 1.1.

Particularly preferred compounds are those in which the different constituents X and Y, or Y and Z, or X, Y and Z, are in equimolar ratio, which is to say that each of the constituents is in a weight proportion of 1, such that the sum of the proportions of each of the constituents is equal to 2 in a salt of two constituents X and Y, or Y and Z, or is equal to 3 in a salt of the three constituents X, Y and Z.

The invention has more particularly for its object compounds selected from the group consisting of arginine α-keto-butyrate, lysine α-keto-butyrate, histidine α-keto-butyrate, arginine α-keto-isocaproate, ornithine α-keto-isocaproate, ornithine α-keto-β methylvalerate, arginine α-keto-β methylvalerate, arginine α-keto-isovalerate, and ornithine α-keto-isovalerate.

The invention also has for its object any pharmaceutical composition comprising, as its active principle, a compound of formula (I) described above, in association with a pharmaceutically acceptable vehicle.

The invention also concerns any pharmaceutical composition comprising, as its active principle, a polyamine of the above-described formula (III), and more particularly cadaverine, putrescine, spermidine, spermine or agmatine, or a compound of the above formula (IV), in association with a pharmaceutically acceptable vehicle.

The pharmaceutical compositions according to the invention are present in a form administrable by oral, parenteral, or rectal route.

Preferably, the pharmaceutical compositions according to the invention are characterized in that the dosage for the active principle is about 0.1 to 50 mg/kg/day, preferably 1 to 20 mg/kg/day by oral and rectal routes, and about 1 μg/kg/day to 10 mg/kg/day by parenteral route.

Preferred pharmaceutical compositions according to the invention are present in the form administrable by oral route, in a unit dosage of 1 mg to 5 g of active principle per dose and preferably 10 mg to 1 g taken in 1 to 4 doses per day. Compositions also preferred according to the invention are present in the form administrable by parenteral route in a unit dose of 50 μg to 500 mg of active principle taken as 1 to 2 injections per day.

The invention has more particularly for its object the use of one or several compounds of formula (I) described above for the preparation of a medication designed for the treatment of human or animal pathologies, in which are involved the silent neurons and more particularly for the symptomatic treatment of pain associated with these pathologies.

The invention also has for its object the use of polyamines of the above-described formula (III) and more particularly of cadaverine, putrescine, spermidine, spermine or agmatine, or the use of compounds of the above formula (IV) for the preparation of a medication adapted for the treatment of the pathologies mentioned above.

Among the above-mentioned human or animal pathologies in which the silent neurons are involved, adapted to be treated by the present invention, can be cited principally the pathologies of the digestive tract, of the bladder and of the biliary ducts, and more particularly the pain associated with these pathologies, of which particularly the pains:

in the trouble of transit and intestinal discomfort associated with intestinal functional troubles (dyspepsia, irritable intestine syndrome, irritable colon . . . )

in the biliary ducts in the rectocolic hemorrhage in the Crohn malady in the gastric or duodenal ulcer in chronic gastritis in colorectal or gastric cancer in gastroenteritis and intestinal flu connected with an intestinal or colic pseudo-obstruction in radical ileitis digestive or visceral post-operative pain in diarrhea, spasms, constipation, megacolon, megarectum in spasms of the bladder in vesical paresis.

The compounds according to the invention can be prepared by dissolving the various constituents in basic form in water. The salt thus obtained in solution in water is then precipitated by means of a solvent miscible with water such as alcohol (methanol, ethanol, isopropanol) or by acetone or acetonitrile, then collected by filtration. The aqueous solution can also be lyophilized.

The solvent obtained in any case can be purified by mixing with a solvent such as diethyl ether or acetonitrile.

The illustration will be further illustrated with the help of the detailed description which follows, of the preparation of compounds of the invention, and their analgesic properties measured on a model of colic distension.

I PROCESSES OF PREPARATION

EXAMPLE 1

Mono-ornithine Keto-glutarate

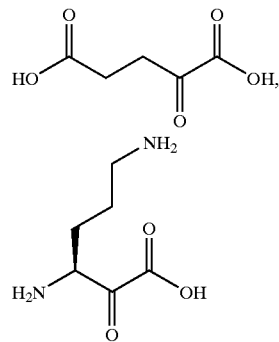

To a basic solution of ornithine in 200 ml of water (1.1 N in water, 20 mmoles, 18.2 ml), α-keto-glutaric acid (2.92 g; 20 mmoles) is added. The solution is frozen and lyophilized one night. It is homogenized in a mortar.

There is recovered 4.7 g (85%) of a white powder.

RMN (D$_2$O): δ 3.75 (t, 1H, CH(NH$_2$)CO$_2$H); 3.1–2.9 (m, 4H, CH$_2$NH$_2$ et CH$_2$COCO$_2$H);2.7 (t, 2H, CH$_2$CO$_2$H ; 2–1.6 (m, 4H, CH—CH$_2$—CH$_2$).

EXAMPLE 2

Di-ornithine Keto-glutarate

Synthesized in the same way as in French patent 3533 M.

EXAMPLE 3

Di-arginine Keto-glutarate

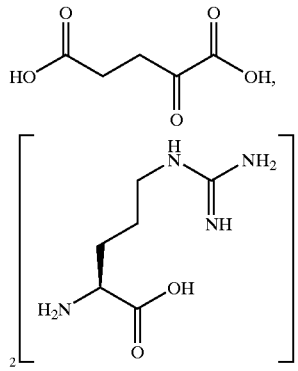

To a solution of L-arginine (10.45; 60 mmoles) in 500 ml of water, is added α-keto-glutaric acid (4.38 g; 30 mmoles). The solution is frozen and lyophilized.

There is obtained a mixture in the form of a foam and of a gum. The foam is removed, browned and screened.

There is recovered 9.26 g (62%) of white powder.

RMN (D$_2$O): δ 3.75 (t, 1H, CH(NH$_2$)CO$_2$H); 3.25 (t, 2H, —CH$_2$NH); 3 (t, 1H, CH$_2$COCO$_2$H); 2.45 (t, 1H, CH$_2$CO$_2$H); 1.9 (m, 2H, CH$_2$CH); 1.65 (m, 2H, CH$_2$CH$_2$NH).

EXAMPLE 4

Ornithine and Arginine Keto-glutarate

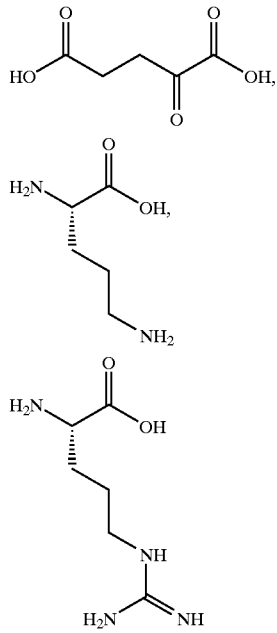

To a basic solution of ornithine (1.1 N in water; 9.1 ml, 10 mmoles) is added α-keto-glutaric acid (1.46 g, 10 mmoles) then L-arginine (1.74 g, 10 mmoles). 100 ml of methanol is added, and there is obtained a gum which is filtered and collected in 100 ml of filtered ethyl ether, filtered and crystallized in 100 ml of acetonitrile.

After filtering, there is recovered 1.53 g of a yellow powder (34%).

RMN (D$_2$O) δ 3.75 (m, 2H, ornithine and arginine CH(NH$_2$)CO$_2$H); 3.2 (t, 2H, CH$_2$NH); 3 (m, 4H, CH$_2$NH$_2$ and CH2COCO$_2$H); 2.5 (t, 2H, CH$_2$CO$_2$H); 2–1.5 (m, 8H, ornithine and arginine CH$_2$CH, CH$_2$CH$_2$NH$_2$, CH$_2$CH$_2$NH).

EXAMPLE 5

Ornithine and Glutamine Keto-glutarate

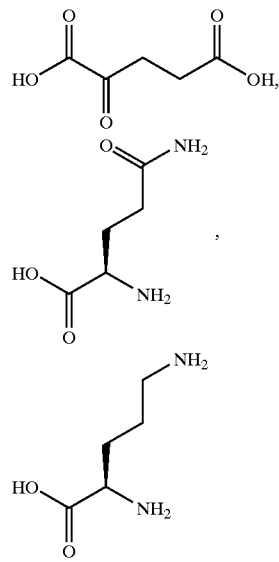

Glutamine (58.4 g, 0.4 moles) and α-keto-glutaric acid (58.4 g, 0.4 moles) are dissolved in 300 ml of water. A 40% solution of ornithine (117 ml, 0.4 moles) is added. 500 ml of ethanol is added, and then this solution is brought to −18° C. to complete crystallization.

This is filtered, washed in acetone and dried under vacuum.

There is obtained 155 g of a white solid (95%).

RMN (D$_2$O): δ 3.75 (m, 2H, ornithine and glutamine CH(NH$_2$)CO$_2$H); 3 (m, 3.5H, CH$_2$NH$_2$ and 1.5 CHCOCO$_2$H); 2.7 (t, 2H, CH$_2$CO$_2$H); 2.5 (m, 2.5H, CH$_2$CONH$_2$ and 0.5 CH$_2$CO$_2$H in hydrated form); 2.15 (m, 2.5H, glutamine CH$_2$CH and 0.5 CH$_2$C(OH)$_2$CO$_2$H); 1.9 (m, 2H, ornithine CH$_2$CH); 1.8 (m, 2H, CH$_2$CH$_2$NH$_2$).

EXAMPLE 6

Mono-ornithine Keto-butyrate

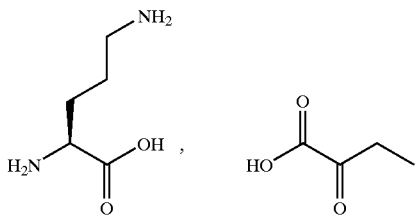

To a solution of ornithine (1.1 N in H$_2$O, 9.1 ml, 10 mmoles) there is added α-keto-glutaric acid (1.02 g, 10 mmoles). 190 ml of acetone is added, it is chilled, filtered, rinsed with acetone and dried under vacuum.

There is obtained 1.07 g of a white solid (46%).

RMN (D$_2$O): δ 3.75 (t, 1H, CH(NH$_2$) CO$_2$H); 3 (t, 2H, CH$_2$NH$_2$); 2.75 (q, 1.5H, CH$_2$CH$_3$); 1.9–1.7 (m, 4.5H, CH$_2$CH and CH$_2$CH$_2$CH and 0.5 CH$_2$CH$_3$ in hydrated form); 1.1 (t, 2.5H, CH$_3$CH$_2$); 0.8 (t, 0.5H, CH$_3$CH$_2$ in hydrated form).

EXAMPLE 7

Ornithine and Spermidine Keto-glutarate

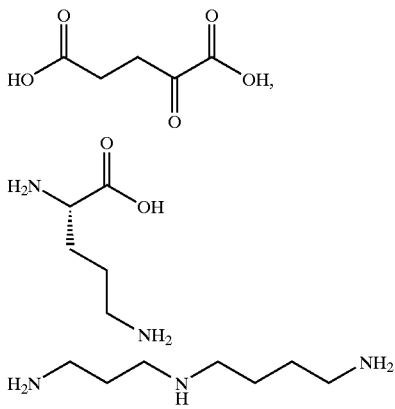

To a basic solution of L-ornithine (1.1 N in H$_2$O, 9.1. ml, 10 mmoles) there is added α-keto-glutaric acid (1.46 g, 10 mmoles) then spermidine (1.45 g, 10 mmoles).

100 ml of methanol and 100 ml of ethyl ether are added. There is obtained a gum which is filtered and collected in acetonitrile. There is recovered 0.9 g of a pale yellow solid (27%).

RMN (D$_2$O): δ 6.7 (m, 0.3H, CHCH$_2$CO$_2$H in enolated form); 3.6 (t, 1H, CH(NH$_2$)CO$_2$H); 3 (m, 10H, ornithine CH$_2$NH$_2$, CH$_2$COCO$_2$H, 4CH$_2$NH$_2$ and spermidine 4CH$_2$NH); 2.4 (m, 0.35H, CH$_2$CO$_2$H); 2.2 (m, 0.75, CH$_2$C(OH)$_2$CO$_2$H); 2–1.6 (m, 11H, CH$_2$CH$_2$CH, CH$_2$CH$_2$CH$_2$NH, CH$_2$CH$_2$NH, CH$_2$CO$_2$H).

EXAMPLE 8

Spermidine Keto-glutarate

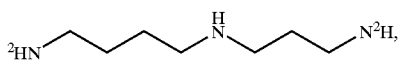

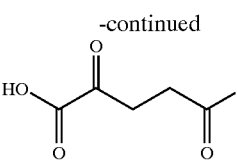

Extemporaneously synthesized by mixing 116.3 mg (0.8 mmole) of spermidine and 117 mg (0.8 mmole) of α-keto-glutaric acid in 50 ml of water, which produces 0.16 M solution.

EXAMPLE 9

Arginine Keto-butyrate

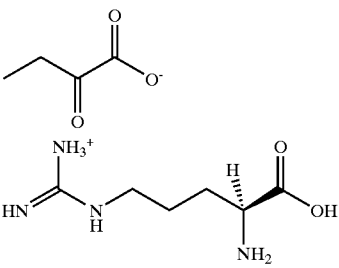

To an acid solution of keto-butyric acid (0.5 g; 4.89 mmoles) in water (2 ml) there is added dropwise a solution of arginine (0.84 g; 4.89 mmoles) in water (10 ml) such that the pH remains below 7.

75 ml of acetone is added, it is decanted and the oil is collected in CH$_3$CN. It is decanted and the obtained paste is again recovered in a keto-nitrile. It is sonicated, titurated one night and then filtered.

There is obtained 0.94 g (70%) of a white solid.

RMN (D$_2$O): δ 3.75 (t, 1H, CH(NH$_2$)CO$_2$H); 3.2 (t, 2H, CH$_2$NH); 2.75 (q, 1.3H, CH$_2$CH$_3$); 2–1.5 (m, 4.7H, CH$_2$CH and CH$_2$CH$_2$CH and 0.7 CH$_2$CH$_3$ in hydrated form; 1.1 (t, 2.3H, CH$_3$CH$_2$); 0.8 (t, 0.7H, CH$_3$CH$_2$ in hydrated form).

EXAMPLE 10

Lysine Keto-butyrate

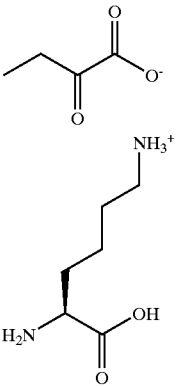

Lysine (1.46 g; 10 mmoles) and oxobutyric acid (1.02 g; 10 mmoles) are dissolved in 5 ml of methanol. Acetone is added, and the precipitate filtered out.

There is obtained 1.36 g (55%) of a white solid.

RMN (D₂O): δ 3.7 (t, 1H, C$\underline{H}$(NH₂)CO₂H); 2.95 (t, 1.7 H, C$\underline{H}_2$NH₂); 2.7 (q, 1.2H, C$\underline{H}_2$CH₃; 1.9–1.2 (m, 6.5H, C$\underline{H}_2$CH and C$\underline{H}_2$CH₂CH and C$\underline{H}_2$CH₂CH₂CH and C$\underline{H}_2$CH₃ in hydrated form); 1 (t, 1.8H, C$\underline{H}_3$CH₂); 0.8 (t, 0.4H, C$\underline{H}_3$CH₂ in hydrated form).

EXAMPLE 11

Histidine Keto-butyrate

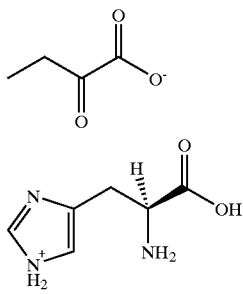

Synthesized in the same way as Example 9.

There is obtained 1.14 g (90%) of a white solid.

RMN (D₂O): δ 8.45 (s, 1H, C$\underline{H}$(N)NH); 7.3 (s, 1H, C$\underline{H}$(C)NH); 4 (t, 2H, C$\underline{H}$(NH₂)CO₂H); 3.3 (dd, 2H, C$\underline{H}_2$CH); 2.7 (q, 1,4H, C$\underline{H}_2$CH₃); 1.7 (q, 0,15H, C$\underline{H}_{CH3}$ in hydrated form; 1,05 (t, 2,2H. CH₂C$\underline{H}_3$); 0,8 (t, 0,3H, CH₂C$\underline{H}_3$ in hydrated form).

EXAMPLE 12

Arginine α-Keto-isocaproate

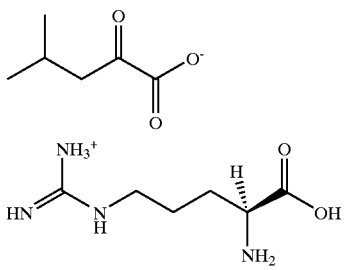

Synthesized in the same was as Example 9.

There is obtained 1.07 g (72%) of a white solid.

RMN (D₂O): δ 3.75 (t, 1H, CH(NH₂)CO₂H); 3,2 (t, 2H, C$\underline{H}_2$NH); 2,6 (d, 2H, C$\underline{H}_2$CO); 2.05 (m, 1H, C$\underline{H}$(CH₃)₂); 1.9–1.5 (m, 4H, CHC$\underline{H}_2$C$\underline{H}_2$); 0.9 (d, 6H, (C$\underline{H}_3$)₂CH).

EXAMPLE 13

Ornithine α-Keto-isocaproate

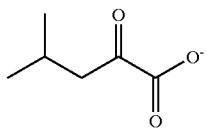

-continued

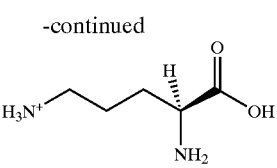

A basic solution of α-keto-isovaleric acid (0.65 g; 5 mmoles) in ornithine (5.95 ml, 111 g/l of H₂O) is prepared. It is concentrated to a third of its volume and 20 ml of acetone is added.

The precipitate it filtered out.

There is obtained 1.07 g (82%) of a white solid.

RMN (D₂O): δ 3.75 (t, 1H, C$\underline{H}$(NH₂)CO₂H); 3 (t, 2H, C$\underline{H}_2$NH₂); 2.6 (d, 1H, C$\underline{H}_2$CO); 2.1 (m, 1H, C$\underline{H}$CH₂CO); 1.9–1.6 (m, 4H, CHC$\underline{H}_2$C$\underline{H}_2$); 0.9 (d, 6H, (C$\underline{H}_3$)₂CH).

EXAMPLE 14

Ornithine α-Keto-β Methylvalerate

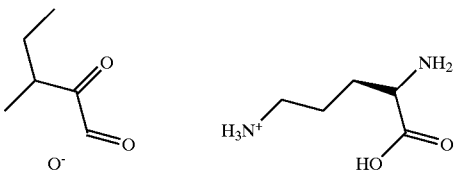

An basic solution of α-keto-β methylvaleric acid (0.65 g; 5 mmoles) and ornithine (5.95 ml, 111 g/l H₂O) is prepared.

It is concentrated to a third of its volume and 60 ml of acetone is added.

The precipitate is filtered out.

There is obtained 1.3 g (78%) of a white solid.

RMN (D₂O): δ 3.75 (t, 1H, C$\underline{H}$(NH₂)CO₂H); 3.05 (t, 2H, C$\underline{H}_2$NH₂); 2.9 (m, C$\underline{H}$CO); 1.9 (m, 2H, CHC$\underline{H}_2$); 1.85–1.4 (m, 4H, C$\underline{H}_2$CH₂NH₂ et CH₃C$\underline{H}_2$); 1.1 (d, 3H, C$\underline{H}_3$CH); 0.9 (t, 3H, C$\underline{H}_3$CH).

EXAMPLE 15

Arginine α-Keto-β Methylvalerate

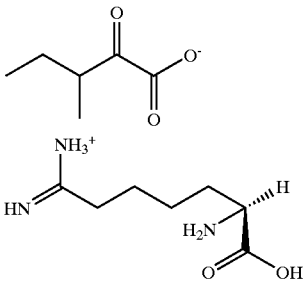

Synthesized in the same way as Example 9.

RMN (D₂O): δ 3.7 (t, 1H, C$\underline{H}$(NH₂)CO2H); 3.2 (t, 2H, C$\underline{H}_2$NH); 2.9 (m, 1H, C$\underline{H}$CO); 1.9 (m, 2H, CHC$\underline{H}_2$); 1.7–1.4 (m, 4H, C$\underline{H}_2$CH₂NH₂ et CH₃C$\underline{H}_2$); 1.1(d, 3H, C$\underline{H}_3$CH); 0.9 (t, 3H, C$\underline{H}_3$CH₂).

EXAMPLE 16

Arginine α-Keto-isovalerate

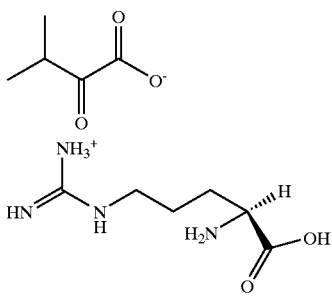

Synthesized in the same way as Example 9.

RMN (D$_2$O): δ 3.7 (t, 1H, CH(NH$_2$)CO2H); 3.2 (t, 2H, CH$_2$NH); 3(m, 0.9H, CH(CH$_3$)$_2$); 1.9–1.5 (m, 4.1H, CH$_2$CH$_2$CH and 0.1 CH(CH$_3$) in hydrated form); 1.1 (d, 5.7H, CH(CH$_3$)$_2$); 0.85 (d, 0.3H, CH(CH$_3$) $_2$ in hydrated form).

EXAMPLE 17

Ornithine α-Keto-isovalerate

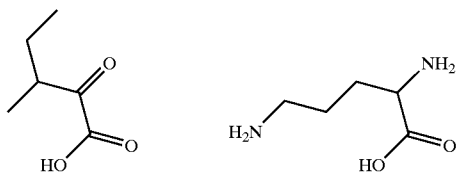

Synthesized in the same way as Example 14.

RMN (D$_2$O): δ 3.7 (t, 1H, CH(NH$_2$)CO$_2$H); 3 (m, 3H, CH$_2$NH$_2$ et CHCO); 1.95–1.6 (m, 4H, CH$_2$CH$_2$CH); 1.1 (d, 6H, CH(CH$_3$)$_2$).

II PHARMACOLOGY

Colic Distension

The analgesic activity was studied on the model of digestive pain in observed rat. This pain is brought about by distension of the colon with a balloon.

Protocol

Male Sprague-Dawley rats of about 180 g, fasted from the day before, are used. Under light fluothane anesthesia, an intrarectal probe is introduced 5 cm into the anus and 1.5 ml of 1% acetic acid is injected. An hour and 30 minutes after irritation, a latex balloon (empty diameter 2 mm, length 1 cm) mounted on a polyethylene catheter is introduced into the colon to the site of the irritation.

The product to be tested or the vehicle (distilled water) is administered per os in a volume of 1 ml, then the rat is observed on a Petri dish.

Distension of the colon is carried out 2 hours and 20 minutes after irritation. It is effected at a fixed volume of 1.5 ml of distilled water. The colic distension gives rise to digestive pain manifested by abdominal cramps whose number reflects the intensity of the pain. The colic distension is maintained for 10 minutes in the course of which the abdominal cramps are counted.

Statistical analysis is carried out with the help of the Dunnett test which compares a same group of vehicle animals (40) to several groups of rats (six animals per group) having received the studied molecules. The threshold of significance is fixed at 5%.

The molecules are tested by the oral route at 1–10–20 mg/kg. They are dissolved in distilled water.

The vehicle used as placebo is comprised by distilled water.

Comparative tests 1 to 5 are products available commercially and are used as such, except ornithine chlorhydrate which is salted out by methods known in the literature and stored in solution in water.

Results

Twenty to twenty-two abdominal cramps, on the average, are observed during 10 minutes of colic distension in the vehicle group of rats (n=40 rats).

The tested molecules significantly decrease (p<0.05) the digestive pain when the number of abdominal cramps is less than or equal to 15.

The results of the compounds according to the invention are given hereafter (Table I).

The compounds according to the invention significantly decrease digestive pain.

TABLE I

Colic distension in rat at 1, 10 and 20 mg/kg p.o.
(Mean number of abdominal cramps ± standard error)

| COMPOUND | PLACEBO (vehicle) | 1 mg/kg | 10 mg/kg | 20 mg/kg |
|---|---|---|---|---|
| α-keto-glutaric acid Comparison 1 | 21 ± 2 | 17 ± 1 | 17 ± 4 | 22 ± 6 |
| Ornithine, HCl Comparison 2 | 22 ± 4 | 20 ± 3 | 19 ± 6 | 18 ± 6 |
| α-keto-butyric acid Comparison 3 | 21 ± 1 | 19 ± 2 | 20 ± 3 | 19 ± 3 |
| Glutamine Comparison 4 | 23 ± 5 | 21 ± 2 | 13* ± 4 | 8* ± 3 |
| Arginine Comparison 5 | 20 ± 1 | 20 ± 6 | 20 ± 9 | 13* ± 6 |
| Mono-ornithine keto-glutarate Example 1 | 20 ± 2 | 11* ± 7 | 11* ± 9 | 15* ± 7 |
| Diornithine keto-glutarate Example 2 | 23 ± 5 | 14* ± 2 | 9* ± 4 | 8* ± 3 |
| Diarginine keto-glutarate Example 3 | 26 ± 9 | 17 ± 9 | 12* ± 4 | 10* ± 5 |
| Ornithine-arginine keto-glutarate Example 4 | 19 ± 1 | 18 ± 2 | 14* ± 9 | 13* ± 5 |
| Ornithine-glutamine keto-glutarate Example 5 | 23 ± 5 | 11* ± 4 | 12* ± 5 | 11* ± 6 |
| Ornithine keto-butyrate Example 6 | 22 ± 1 | 12* ± 5 | 14* ± 7 | 8* ± 3 |
| Spermidine ornithine keto-glutarate Example 7 | 21 ± 2 | 13* ± 2 | 14* ± 3 | 9* ± 4 |
| Spermidine-keto-glutarate Example 8 | 18 ± 0.7 | 8* ± 4 | 9* ± 4 | 8* ± 2 |

*Statistically different from the placebo at p < 0.05 (Dunnett test)

What is claimed is:

1. A method for the treatment of human or animal pathologies in which the silent neurons are involved, comprising administering to a human or animal in need of same a therapeutically effective amount of a salt of the following general formula (I):

$$(X)_{n1}, Y, (Z)_{n2} \qquad (I)$$

in which:

$n_1$ and $n_2$ represent 0 or 1, provided that when $n_1=0$ then $n_2=1$, and when $n_2=0$ then $n_1=1$, X represents a natural amino acid, provided that when $n_2=0$ then X is a basic amino acid, Y represents a keto acid of the following formula (II):

R—CO—COOH (II)

in which R represents an alkyl or alcanoic acid, substituted or not, of about 1 to about 10 carbon atoms, Z represents:
- a natural amino acid,
- or, a polyamine comprising at least two primary, secondary or tertiary amine functions, spaced by a linear or branched hydrocarbon chain of about 3 to 10 carbon atoms.

2. The method according to claim 1, in which:

$n_1=1$, and $n_2=0$ or 1,

X represents an amino acid selected from ornithine, arginine or glutamine,

Y represents a keto acid selected from α-keto glutaric acid or α-keto butyric acid, and, when $n_2=1$, Z represents:
- a natural amino acid,
- or a polyamine of formula (III):

$R_1$—HN—$(CH_2)n$-NH—$R_2$ (III)

in which:

n represents a whole number comprised between 4 and 5, and when n=4,
$R_1$ and $R_2$ represent H,
or, $R_1$ represents H and $R_2$ represents $(CH_2)_3NH_2$,
or, $R_1$ and $R_2$ represent $(CH_2)_3NH_2$, when n=5,
$R_1$ and $R_2$ represent H,
or, $R_1$ represents H and $R_2$ represents a group of the formula

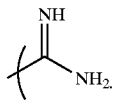

3. The method according to claim 1, in which:

$n_1=1$, and $n_2=0$,

X represents ornithine and Y represents α-keto glutaric acid,

X represents ornithine and Y represents α-ketobutyric acid,

X represents arginine and Y represents α-ketobutyric acid,

X represents lysine and Y represents α-ketobutyric acid,

X represents histidine and Y represents α-ketobutyric acid,

X represents arginine and Y represents α-ketoisocaproate acid,

X represents ornithine and Y represents α-ketoisocaproate acid,

X represents ornithine and Y represents α-keto-β methylvalerate acid,

X represents arginine and Y represents α-keto-β methylvalerate acid,

X represents arginine and Y represents α-keto-isovaleric acid,

X represents ornithine and Y represents α-keto-isovaleric acid.

4. The method according to claim 1, in which:

$n_1=1$, and $n_2=1$,

X represents ornithine, Y represents α-keto-glutaric acid, and Z represents ornithine, X represents arginine, Y represents α-keto-glutaric acid, and Z represents arginine, X represents ornithine, Y represents α-keto-glutaric acid, and Z represents glutamine, X represents ornithine, Y represents α-keto-glutaric acid, and Z represents spermidine.

5. The method according to claim 1, wherein said salt is diornithine α-keto-glutarate.

6. The method according to claim 1, in which:

$n_1=0$ or 1, and $n_2=1$, when $n_1=1$, X represents a natural amino acid,

Y represents a keto acid selected from α-keto-glutaric acid or α-keto-butyric acid, Z represents a polyamine of formula (III) above.

7. The method according to claim 1, in which $n_1=0$ and $n_2=1$, Y represents α-keto-glutaric acid and Z represents spermidine.

8. The method according to claim 1, in which said salt is in the form of a salt between two constituents X and Y, or Y and Z, or between the three constituents X, Y and Z.

9. The method according to claim 1, in which the weight proportion of the different constituents of X.Y.2 of said salt comprise between 0.8 and 1.2, such that the sum of the proportions of each of the constituents is equal to 2 in a salt between two constituents, or is equal to 3 in a salt between three constituents.

10. The method according to claim 1, in which the different constituents X and Y, or Y and Z, or X, Y and Z of said salt are in an equimolar ratio, which is to say that each of the constituents is in a weight proportion of 1, such that the sum of the proportions of each of the constituents is equal to 2 in a salt between two constituents X and Y, or Y and Z, or is equal to 3 in a salt between the three constituents X, Y and Z.

11. A salt of the following general formula (IV):

$(X)_{na},(Y)_{nb},Z$ (IV)

in which:

$n_a$ and $n_b$ represent 0 or 1, with the proviso that when $n_a=0$ then $n_b=1$, and when $n_b=0$ then $n_a=1$, X represents a natural amino acid, Y represents a keto acid of the following formula (II):

R—CO—COOH (II)

in which R represents an alkyl or alcanolic acid group, substituted or not, of about 1 to about 10 carbon atoms, Z represents a polyamine comprising at least two primary, secondary or tertiary amine functions, spaced by a linear or branched hydrocarbon chain of about 3 to 10 carbon atoms.

12. The salt according to claim 11, of the general formula (IV) in which $n_a=0$ and $n_b=1$, Y represents α-keto glutaric acid, and Z represents spermidine.

13. A pharmaceutical composition characterized in that it comprises a salt according to claim 11, in association with a pharmaceutically acceptable vehicle.

* * * * *